United States Patent [19]

Wilson

[11] Patent Number: 4,488,320
[45] Date of Patent: Dec. 18, 1984

[54] PROSTHETIC HIP

[75] Inventor: Michael T. Wilson, Missouri City, Tex.

[73] Assignee: Medical Center Prosthetics, Inc., Houston, Tex.

[21] Appl. No.: 456,617

[22] Filed: Jan. 10, 1983

[51] Int. Cl.³ ............................ A61F 1/08; A61F 1/04
[52] U.S. Cl. .................................................. 3/15; 3/21
[58] Field of Search ............................ 3/15, 17 R, 21, 2

[56] References Cited

U.S. PATENT DOCUMENTS 4,215,441  8/1980  Wilson ........................................ 3/15

OTHER PUBLICATIONS

Otto Bock endoskeletal prosthesis-known extremity components System Overview.

Primary Examiner—Ronald L. Frinks
Attorney, Agent, or Firm—Phillips, Moore, Lempio & Finley

[57] ABSTRACT

An improved flexion biased prosthetic hip includes an extended biasing spring to permit hyperextension of the joint relative the frontal plane of the user. In addition, a bifurcated actuator rod is disclosed. This actuator rod transmits the biasing force of the extended biasing spring from a collar surrounding the leg pylon to the hip mounting plate. The bifurcated actuator rod eliminates the binding associated with the previously used actuator members that were formed as a plate with a roller contacting the pylon.

3 Claims, 7 Drawing Figures

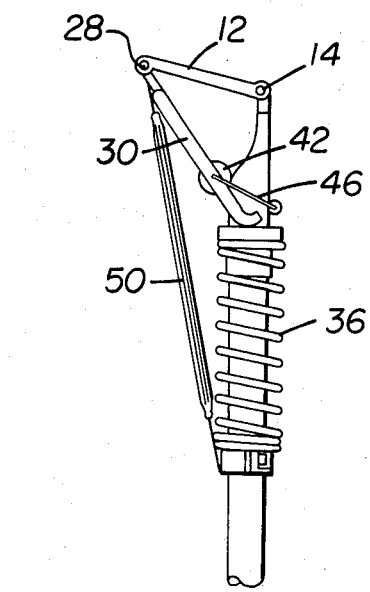
FIGURE 2
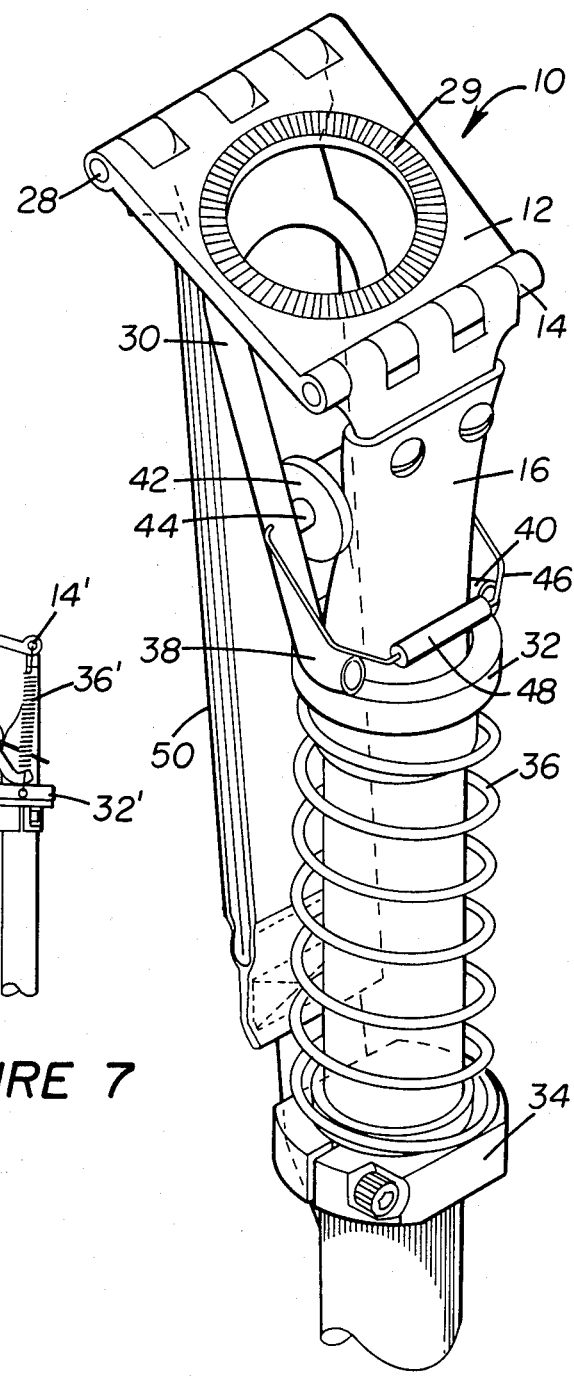
FIGURE 1
FIGURE 7
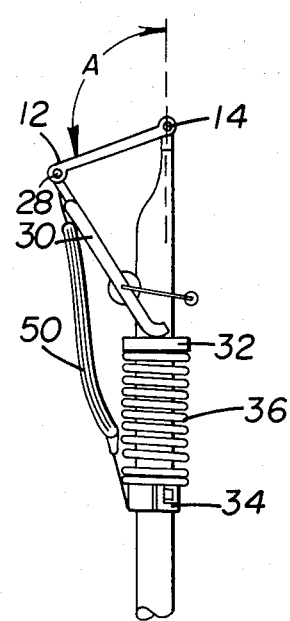
FIGURE 3

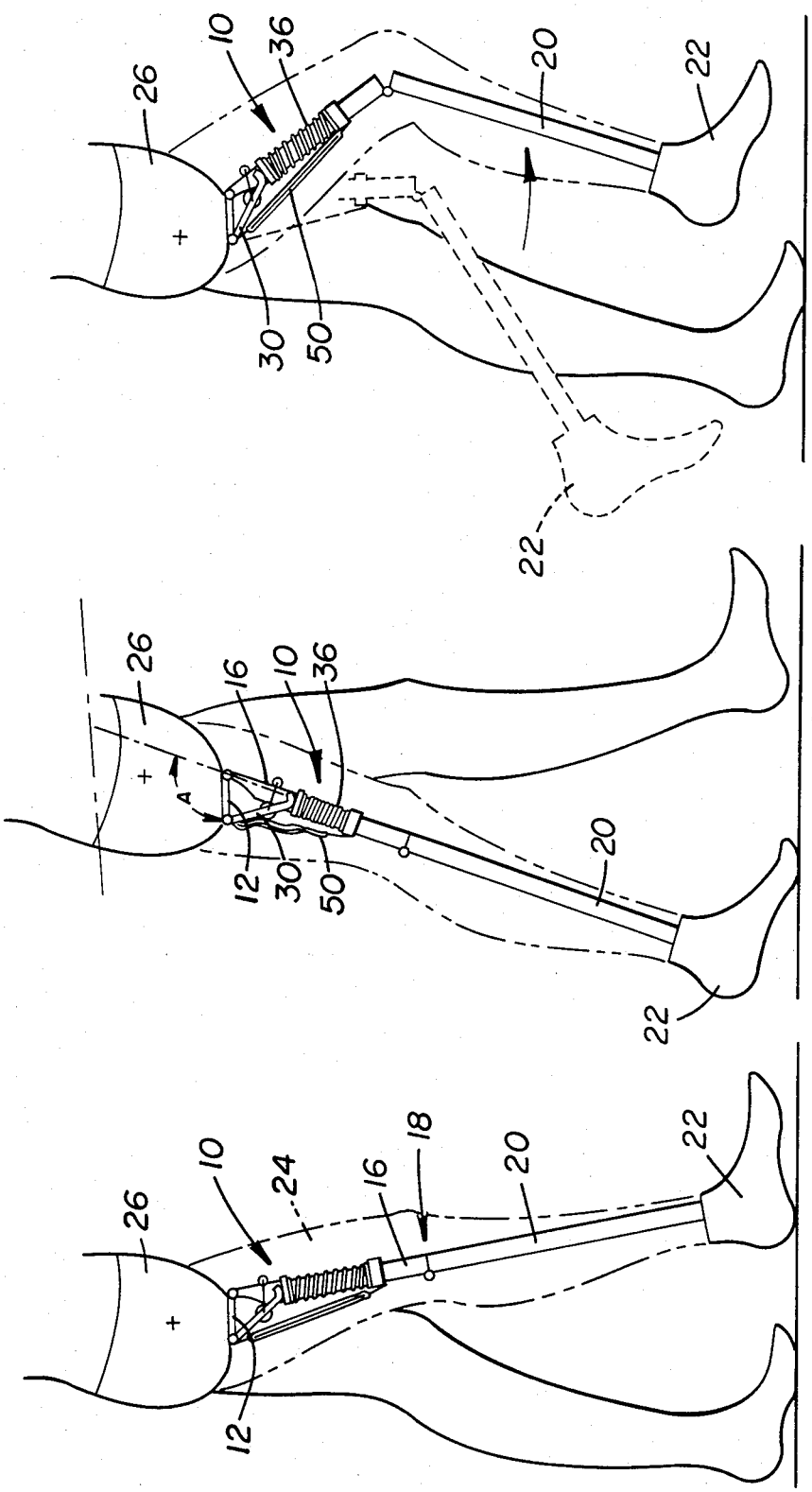

PROSTHETIC HIP

This invention relates to a prosthetic device. Specifically, it relates to an improved prosthetic hip joing for use with an entire leg replacement.

Removal of a portion of the pelvis carries with it the concomitant loss of the hip joint. Such removal may result from trauma or disease. Unfortunately, loss of the hip joint takes with it the loss of the musculature of the leg. The muscles of the leg and the hip are important if any motion at all is to be imparted to a prosthesis to enable a patient to walk again.

Presently, there are available at least two types of jointed hip prostheses that may be used in lieu of the hip joint of an amputee. The first type biases the artificial leg to the frontal plane of the user and thus requires considerable energy expenditure to swing the artificial leg. The second, which is described in U.S. Letters Pat. No. 4,215,441 issued Aug. 5, 1980 to the inventor herein and assigned to the assignee of this invention, flexion biases the artificial leg to a position anterior of the frontal plane of the user. This hip joint, when used in conjunction with a weight-actuated locking knee joint, permits a much more fluid gait. Further, the flexion biasing reduces the energy requirement to a great extent.

Unfortunately, both the conventional frontal biased and the flexion biased hips have a tendency to bind after a period of use because the actuator member or plate that transmits the biasing force to the mounting plate bears on only one spot on the collar surrounding the pylon. Further, both of the prior art hips permit only anterior articulation of the joint, thus generally preventing hyperextension. While such limited articulation is satisfactory, it generally results in a gait with an evident hike to the body as the leg passes the frontal plane. A natural hip joint, due to the motion of the pelvis and also due to the fact that a natural hip permits a certain degree of hyperextension of the leg, does not show this hike during a walking gait.

It is an object of the present invention to provide a flexion biased hip joint which includes a capability to hyperextend during a normal walk phase.

It is a further object of the invention to provide a prosthetic hip joint that overcomes the binding tendencies of previous hip joints. It is still another object of this invention to include the hyperextension features with the previously-known flexion biased prosthetic hip joints.

SUMMARY OF THE INVENTION

Specifically, this invention is an improved flexion biased prosthesis that includes an upper limb pylon and a bearing plate adapted for mounting on a hip socket. The improvement includes a hinged element pivotally fixing the upper limb pylon to the bearing plate and capable of permitting the pylon to hyperextend relative the bearing plate. The improvement also includes a resilient member for biasing the pylon to a fixed position.

BRIEF DESCRIPTION OF THE DRAWINGS

FIG. 1 is a perspective view of the prosthetic hip wich forms an embodiment of this invention.

FIG. 2 is an elevational view of the prosthesis in the flexed position.

FIG. 3 is a view of the same prosthesis in the hyperextended position.

FIG. 4 shows the prosthesis in use in the flexed position with the leg fully extended.

FIG. 5 shows the prosthesis in the hyperextended position relative the body at the toe-off position.

FIG. 6 is a composite view of the prosthesis as its swings toward the flexed position.

FIG. 7 is an alternate embodiment of the prosthesis shown in the FIG. 1.

DETAILED DESCRIPTION OF THE PREFERRED EMBODIMENT

Referring to FIG. 1, a flexion biased prosthesis hip 10 is illustrated in the flexed position. Hip 10 includes a bearing plate 12 that is hinged at hinge 14 to a pylon 16 that forms the upper limb of a prosthetic leg. Referring briefly to FIG. 4, it can be seen that fixed to pylon 16 is a knee joint 18 having affixed to it a lower limb pylon 20. Pylon 20 has affixed at its lower end a prosthetic foot 22. Knee joint 18 is preferably a specially-configured weight actuated knee joint that is available from the Otto Bock Company of West Germany and is designed so that upon heel contact of an associated prosthetic foot 22, force applied to the upper limb 16 through the knee joint locks the knee. As the prosthesis passes through mid-stance, the knee joint mechanically unlocks, yet remains biomechanically locked to the point of heel-off, at which time the knee is free to flex. Finally, the entire prosthesis may be encased in a light-weight cosmesis 24 shaped for aesthetic purposes. The prosthesis is associated with the body of the user by means of a hip socket 26 to which the bearing plate 12 is affixed. It can be seen that bearing plate 12 has a series of index marks 29 which facilitate location of the prosthesis to the hip socket.

Bearing plate 12 has fixed at the end distal of hinge 14 a second hinge 28 to which a bifurcated actuator member 30 is affixed. Bifurcated member 30 extends downwardly toward pylon 16 and engages a slidable collar 32 which is mounted about pylon 16 as shown in FIG. 1. A second collar 34 is adjustably fixed to pylon 16 below collar 32 so that a helical spring or an equivalent resilient member 36 may bias collar 32 upwardly on pylon 16 away from collar 34. The result of this biasing is to position the bearing plate 12 at an angle relative to pylon 16. Referring to FIG. 4, it can be seen that the result of this angular biasing of bearing plate 12 results in a flexed position of the artificial hip joint so that pylon 16, in its biased position, is approximately twenty degrees forward of the frontal plane of the patient.

Actuator member 30 is bifurcated so that each tine 38 and 40 of the bifurcation rests on collar 32 at positions generally diametrically opposed, thereby reducing the probability of the actuator 30 or collar 32 binding in a position such that the prosthesis remains in the flexed position or some intermediate position between the positions shown in FIG. 4 and 5. Included in the bifurcation is a roller 42 which is mounted on an axle 44 extending between tine 38 and tine 40. The purpose of roller 44 is to guide the actuator upwardly and downwardly relative to the pylon 16. As can be seen from FIGS. 2 and 3, the relative positioning of actuator 30 and bearing plate 12 is such that the actuator will remain in the same general position relative to collar 32 as long as roller 42 is positioned as indicated. Also included is a bail 46 mounted coaxially with axle 44 and extending out and around pylon 16. Bail 46 serves the purpose of retaining the actuator member 30 on collar 32 in the unlikely event contact is lost between tines 38 and 40 and collar 32 which might result in actuator 30 dropping away from pylon 16. A roller 48 is positioned on bail 46 to facilitate movement upwardly and downwardly of the bail relative pylon 16.

Finally, a resilient strap 50 interconnects bearing plate 12 and lower collar 34. It should be noted that resilient strap 50 is fixed bearing plate 12 at the intersection of actuator 30 and bearing plate 12.

Referring now to FIG. 3, it can be seen that bearing plate 12 is in the position the prosthesis would take when it was hyperextended. It should be noted that there still remains spring travel in spring 36. In previous prosthetic hips of either the flexion biased type or the frontal plane variety, hyperextension of the hip joint had not been permitted, at least to the degree permitted in this invention. It has been found that bearing plate 12 should be able to hyperextend to about 120°. This angle is illustrated in FIGS. 3 and 5 as angle A and is measured from the axis of pylon 16 to the angle of the bearing plate. It will be noted in FIGS. 4, 5 and 6 that bearing plate 12 remains generally parallel to the transverse plane of the body of the amputee, while in earlier hip prostheses, the comparable angle A would not exceed 90°, thus resulting in a hike in the gait of the user.

APPLICABILITY

Referring now to FIGS. 4, 5, and 6, the prosthesis 10 is shown in operation. It is, of course, assumed that a portion of the pelvis of the amputee has been removed and that hip socket 26 is the mounting portion fixed to the amputee. Of course, hip socket 26 is formed to fit the body of the amputee. Bearing plate 12 is then positioned by the prosthetist at the lower end of socket 26. It will be remembered that bearing plate 12 is formed with index marks 29 to facilitate the orientation of prosthetic hip 10. Those skilled in the art will understood that the swing of the appended leg must be substantially in the sagittal plane of the user. Otherwise, the body will swing or rotate during walking. Thus, rotation of the leg about the axis of the pylons may be necessary during fitting.

In operation, the prosthesis will take on the position approximately as shown in FIG. 4 at the time of heel contact. As noted above, knee joint 18 is mechanically locked upon heel contact and remains mechanically locked until the line connecting the center of gravity of the body to the point of contact on the ground passes through the knee joint and moves forward of the knee. This generally occurs at heel off which is not shown in the illustrations but would occur some time just before position shown in FIG. 5. At heel off, the knee is biomechanically locked because of the orientation of the center of gravity to the point of contact on the ground. In previous joints, bearing plate 12 would remain substantially perpendicular to pylon 16 once the leg passed through the vertical position. In this invention, as seen in FIG. 5, the bearing plate remains generally parallel to the transverse plane T throughout the walk phase. This is accomplished by positioning collars 32 and 34 sufficiently far apart to permit a longer spring travel.

It will be noted that during the gait of the walker the force stored in spring 36 is transmitted to the bearing plate 12 by the actuator 30. Referring now to FIG. 6, the amputee is shown placing his weight on his left leg and removing his weight from the prosthesis. When this occurs, the spring 36 acting through the actuator arm 30 flexes the hip to a position shown generally in FIG. 6. The inertia of the foot 22 intially flexes the lower limb or pylon 20. However, when strap 50 halts the flexion of the hip joint, the same inertia acts on foot 22 and the lower pylon 20 to swing it forwardly. The amputee then makes heel contact with the prosthesis at the time the lower pylon 20 and the upper pylon 16 are in a straight line. By placing weight on the heel of foot 22, the knee 16 is locked and the sequence started again as shown at FIG. 4.

Should the amputee be seated and wish to begin walking, the amputee would stand and bend at the waist so that the prosthesis would take on a straight line orientation such as shown in FIG. 4. Once the prosthesis is in the straight line position, a weight can be placed on the heel and the weight activated knee then operates in the manner previously described.

This improvement over previous prosthetic hip joints permits a more natural gait, eliminating the hike that occurs when hyperextension of the joint is precluded. Furthermore, by making actuator 30 contact collar 32 on diametrically opposed sides results in no binding of the actuator or of the collar.

ALTERNATE EMBODIMENT

Referring now to FIG. 7, an alternate embodiment of the prosthesis just described is shown herein. The structure of the alternate embodiment is substantially the same as previously described. However, the resilient member 36 is no longer positioned below the collar 32. In this embodiment a pair of springs 36' are positioned outside the bifurcated actuator 30 (only one spring is shown in FIG. 7). These springs are tension springs rather than compression springs as shown in the primary embodiment. Strap 50', which had been interconnected to collar 34, may now be positioned on thesliding collar 32' or conversely, affixed to the pylon at some point well below the sliding collar 32'. It also should be noted that in this embodiment, the springs should have equal spring constants to avoid binding of the collar.

While two arrangements have been illustrated to show that the resilient member 36 can be positioned in different locations, it should also be noted that the resilient member could be positioned inside the pylon with a piston-like member replacing collar 32 and a pin extending outwardly of the slots running down each side of pylon 16.

Operation of the alternate embodiment is the same as the primary embodiment and thus no further discussion is considered necessary.

Other aspects, objects, and advantages of this invention can be obtained from a study of the drawings, the description and the appended claims.

I claim:
1. An improved flexion biased prosthesis including an upper limb pylon, and a bearing plate adapted for mounting on a hip socket, the improvement comprising:
   hinge means for pivotally fixing the upper limb pylon to the bearing plate and capable of permitting said pylon to hyperextend relative said bearing plate;
   resilient means for biasing said pylon to a flexed position, said resilient means including a moveable collar disposed about said pylon and a resilient member fixed at one end relative to said pylon and fixed at its other end to said collar so that said collar is biased toward the bearing plate; and,
   an actuator member hingedly fixed at one end to said bearing plate distal of the pylon and engageable at said collar to transmit the biasing force to said bearing plate, said actuator member being bifurcated and having legs extending past the center line of each side of the pylon so that the points of engagement with the collar by each leg are generally diametrically opposite.

2. The improvement of claim 1 wherein the actuator rod further includes an axle interconnecting the bifurcations and a positioning roller mounted on said axle for rolling contact with the pylon.

3. The improvement of claim 1 wherein the actuator rod further includes a U-shaped bail pivotally fixed to the bifurcations and circling the pylon distal of the hinged connection of the link and the plate.

* * * * *

UNITED STATES PATENT AND TRADEMARK OFFICE
CERTIFICATE OF CORRECTION

PATENT NO. : 4,488,320
DATED : December 18, 1984
INVENTOR(S) : MICHAEL T. WILSON It is certified that error appears in the above-identified patent and that said Letters Patent is hereby corrected as shown below:

Col. 1 Line 5 correct spelling --joint-- vice "joing"

Col. 1 Line 66 correct spelling --which-- vice "wich"

Col. 2 Line 14 correct spelling --prosthetic-- vice "prosthesis"

Col. 2 Line 25 insert --the-- between "22," and "force"

Col. 3 Line 9 insert --to-- between "fixed" and "bearing"

Col. 3 Line 39 change "understood" to --understand--

Col. 3 Line 56 insert --the-- between "joints," and "bearing"

Col. 4 Line 15 change "the" first occurrence to --this--

Col. 4 Line 36 change "theslid" to read --the slid--

Signed and Sealed this

Thirtieth Day of April 1985

[SEAL]

Attest:

DONALD J. QUIGG

Attesting Officer     Acting Commissioner of Patents and Trademarks